US005704891A

United States Patent [19]

Mussivand

[11] Patent Number: 5,704,891

[45] Date of Patent: Jan. 6, 1998

[54] ELECTROHYDRAULIC VENTRICULAR ASSIST DEVICE

[75] Inventor: Tofy Mussivand, Ottawa, Canada

[73] Assignee: Ottawa Heart Institute Research Corporation, Canada

[21] Appl. No.: 451,522

[22] Filed: May 26, 1995

Related U.S. Application Data

[62] Division of Ser. No. 303,766, Sep. 9, 1994, Pat. No. 5,569, 156.

[30] Foreign Application Priority Data

Sep. 10, 1993 [CA] Canada ........ 2105908
Sep. 10, 1993 [CA] Canada ........ 2105935

[51] Int. Cl.[6] ........ A61N 1/362

[52] U.S. Cl. ........ 600/16; 623/3

[58] Field of Search ........ 600/16–18; 623/3

[56] References Cited

U.S. PATENT DOCUMENTS

| | | | |
|---|---|---|---|
| 3,744,243 | 7/1973 | Faisandier | 60/431 |
| 3,919,722 | 11/1975 | Harmison | 3/1.7 |
| 4,173,796 | 11/1979 | Jarvik | 3/1.7 |
| 4,222,127 | 9/1980 | Donachy et al. | 3/1.7 |
| 4,397,049 | 8/1983 | Robinson et al. | 3/1.7 |
| 4,547,991 | 10/1985 | Searcy | 43/18.1 |
| 4,588,404 | 5/1986 | Lapeyre | 623/3 |
| 4,704,120 | 11/1987 | Slonina | 623/3 |
| 4,781,715 | 11/1988 | Wurzel | 623/3 |
| 4,820,301 | 4/1989 | Chareire et al. | 623/3 |
| 4,838,889 | 6/1989 | Kolff | 623/3 |
| 4,888,011 | 12/1989 | Kung et al. | 623/3 |
| 4,976,729 | 12/1990 | Holfert et al. | 623/3 |
| 4,981,484 | 1/1991 | Holfert et al. | 623/3 |
| 5,089,016 | 2/1992 | Millner | 623/3 |
| 5,089,018 | 2/1992 | Lapeyre et al. | 623/3 |
| 5,089,020 | 2/1992 | Koppert | 623/3 |
| 5,133,743 | 7/1992 | Strimling | 623/3 |

FOREIGN PATENT DOCUMENTS

| | | | |
|---|---|---|---|
| 1188852 | 6/1985 | Canada | 3/116 |
| 2007439 | 1/1990 | Canada | 326/15 |
| 2047534 | 7/1991 | Canada . | |
| 2 239 802A | 1/1990 | United Kingdom . | |

*Primary Examiner*—John P. Lacyk
*Attorney, Agent, or Firm*—Leonard Bloom

[57] ABSTRACT

A unified system for implantation in the thorax and for cannulation to the blood circulatory system comprises an electronic controller for generating an actuating signal and an energy convertor for converting the actuating signal into a back and forth rhythmic displacement of the blood between a blood pumping chamber (BPC) and a volume displacement chamber (VDC). The BPC has an inflow port and an outflow port and converts the back and forth displacement into a rhythmic unidirectional displacement of blood from the inflow to the outflow port. The actuating signal is generated by a detector in response to the status of the BPC. A support unitary with the VDC supports the internal electronic controller, the actuating means, the BPC, and the detecting means in a compact structure and has a surface curvature compatible with the internal human sagittal and transverse chest wall curvatures. The BPC is arranged with the inflow and outflow ports oriented away from the support for ready cannulation to the circulatory system.

29 Claims, 9 Drawing Sheets

OUTSIDE OF BODY
INSIDE OF BODY
EXTERNAL BATTERY
TO POWER SOURCE
SKIN
INTERNAL BATTERY
COMPUTER
EXTERNAL CONTROLLER
INTERNAL CONTROLLER
IRD
TET
TELEMETRY
TET
TELEMETRY

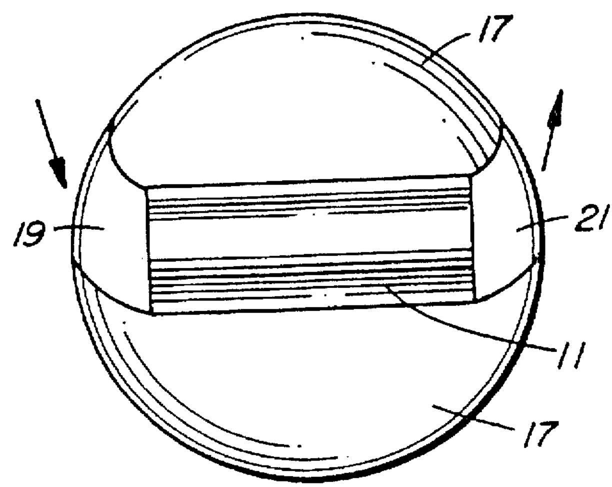
FIG. 7a
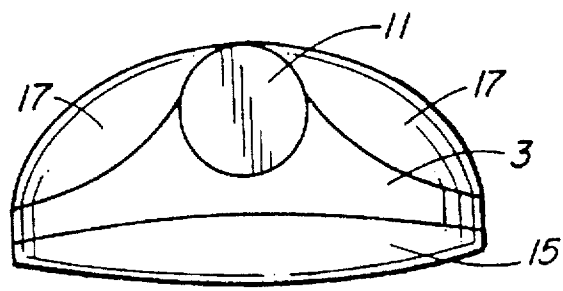
FIG. 7b
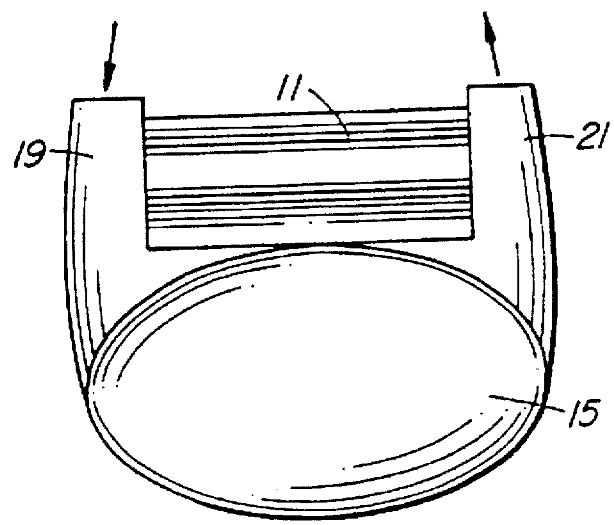
FIG. 8a
15
3
17
FIG. 8b

ELECTROHYDRAULIC VENTRICULAR ASSIST DEVICE

This application is a division of application Ser. No. 08/303,766, filed Sep. 9, 1994 now U.S. Pat. No. 5,569,156.

BACKGROUND OF THE INVENTION

1. Field of the Invention

The present invention relates to the field of equipment and prothesis as a circulatory device aid for assisting or replacing the right and/or the left ventricle of the natural heart. More particularly, this invention is concerned with an electrohydraulic ventricular assist device which integrates several of the major components required for this type of device into one component herein referred to as the Unified System which is implantable into the human thorax.

2. Description of the Related Art

Cardiac transplantation using a natural heart taken from a donor and grafting it into a recipient is now a relatively routine surgical technique. Recent advances have resulted in an appreciable reduction of rejection. However, practical transplantation is limited to the availability of natural heart donors and effective immunosuppressive drugs.

Clinical experience has shown that the cardiovascular circulation of patients in severe or total heart failure can be sustained with proper right and left ventricular assist devices (RVAD and LVAD).

For these and other reasons, a number of mechanical circulatory devices have been designed to replace and/or assist the diseased natural heart. Total artificial hearts (TAH) and ventricular assist devices (VAD) have been valuable clinical tools in recent years with their primary benefit as a bridge to transplantation following acute cardiac failure. Currently many of these devices are large requiring multiple implant sites for various components and long tubes and wires to connect these various components, thus they must be located in the abdominal cavity or outside the body.

For serious cases of heart failure, one should aim for long tern support rather than support limited in weeks, days or hours. In addition, it is preferable to have an assisting device which can be used for both left and/or right ventricular support. Typically, devices for assisting the left ventricle are located in the abdominal cavity or outside the chest. Traditional artificial hearts fit less than ideally inside the chest.

Generally, the requirements for a ventricular assist device are multiple and not easy to satisfy, It is desirable that such device be implanted in the thoracic cavity. The intra-thoracic blood pumping components of the device must be similar in size and weight to the natural heart. The artificial heart life must be sufficiently long and the reliability sufficiently high to avoid the risk of sudden prosthesis failure. The formation of adherent thrombus must be prevented. Thromboemboli and extensive blood damage must also be prevented. The device must not damage adjacent tissue or traumatize adjacent organs by compression or by excessive local temperatures. The artificial hearts must also avoid skin penetration by connections to the exterior to prevent infections. As well, shortening of the length of the artificial blood vessels or cannulae employed for connecting the device to the natural heart or circulatory system is another desirable requirement for the device.

There has been a great deal of development activity in the area of artificial hearts, and especially for devices to assist the left ventricle (LVADs). Generally, a ventricular assist device comprises an elastomeric blood chamber or diaphragm capped cavity. The blood chamber is provided with an inflow and an outflow valve for connection to the circulatory system. The blood chamber volume is controlled with the elastomeric diaphragm which is actuated to oscillate between a systolic and a diastolic position.

To transform electrical power generated outside the body into the rhythmic movement of the diaphragm while obtaining suitable values for the above parameters and thermodynamics, various types of energy convertors have been tested.

The displacement of the diaphragm is obtained by various methods. Among these, electrohydraulic operation of the diaphragm proves to be a dependable and reliable method. Electrohydraulic ventricular assist devices are provided with a pump which displaces a hydraulic fluid (oil) between a fluid reservoir and a fluid chamber, which is adjacent with the blood chamber so as to share the elastomeric diaphragm. The rhythmic fill and drain of the oil, in and out of the fluid chamber, displaces the diaphragm which in turn moves the blood in and out the blood chamber.

Canadian Patent No. 1,188,852 (Robinson) discloses a hydraulically actuated cardiac prosthesis with a hydraulic fluid reservoir, a hydraulic fluid pumping means and a blood pumping chamber with a flexible diaphragm. U.S. Pat. No. 4,222,127 (Donachy et al.) discloses the Pierce-Donachy artificial heart including a blood pump, flexible diaphragm and an inflow and an outflow valves which can be used paracorporeally or intra-thoracically. U.S. Pat. Nos. 4,588,404 (Lapeyre) and 5,089,018 (Lapeyre et al.) disclose a biventricular cardiac prothesis. The device is a sealed case with a dual membrane system for pumping the systemic and pulmonary circulations.

However, a major limitation of these past devices is their physical shape, size and complexity which increase the surgical difficulty of implanting the device in either the thorax or abdomen of a patient. Power and information transfer requirements of the past devices have also required percutaneous access to the implantation site with its associated risk of infection. These limitations have also had an effect on the length of time that these devices can be implanted.

Recently, devices for establishing communication of electrical signals between the implanted device and an external power source and electronics controller have been developed as disclosed in Canadian Patent application No. 2,007,439 {(2,074,150} (Miller) and U.K Patent No. 2239802E (Miller). Such transcutaneous energy transformers employ electromagnetic induction using a pair of coupled coils, one outside and one inside the patient body. The ventricular assist device then can have an internal control mechanism for adjusting the frequency of oscillation of the diaphragm. To maintain maximum power transfer as the coils move relative to one another, a phase locked loop system in the external power converter maintains a constant phase relationship between voltage and current in the primary coil, thus minimizing voltage fluctuations. This was disclosed by Mussivand et al. (Performance evaluation of a transcutaneous energy transfer system, ASAIO Abstract 21:39, 1992). These patents and this article are incorporated by reference.

The bidirectional communication of information between the implanted device and its portable external control unit is achieved by an infrared data link. Data is transmitted across the skin without perforating it using a standard synchronous data transmission protocol. This protocol awards hardware compatibility with any computer having an RS232 type interface. It was disclosed by Miller J. et al. (Performance Evaluation of a transcutaneous infrared telemetry system, ASAIO Abstr 21:39, 1992).

An ideal artificial heart device should integrate the major pumping and controlling components into a single Unified System for reducing the length of the electrical connections and of fluid conduits. There are also requirements for a material that should be accepted by the human body. Fluid dynamics of the device should not cause thrombus formations and the potential for thromboemboli.

Anatomical fit has a significant impact on the case of surgical implantation, organ compression, patient comfort and postoperative complications. The internal body cavity dimensions have been recognized as a prime limitation in the design of implantable, mechanical circulatory devices.

To date no comprehensive fundamental system has been patented that provides for the integration of the major components into a compact, lightweight, totally implantable unit which can be implanted in the chest cavity.

OBJECTS OF THE INVENTION

It is an object of the present invention to provide a totally implantable circulatory device which integrates the major components of the system into a single Unified System which is small enough to implant in a patient's body without giving rise to any serious clinical disadvantage or inconvenience to the recipient's organs. This integration will result in a reduction of the number of surgical sites. The device of the present invention takes into account the best location for implantation in the patient and the best shape which is compatible with this location.

It is another object of the present invention to provide a ventricular assist device which can be fixed into the human chest in the proximity of the natural heart thereby shortening the length of the artificial blood vessels or cannulae employed for connecting the device to the natural heart. This will result in a reduction in cannulation lengths to the natural heart, thus reducing hydraulic resistance, kinking, turbulence, separation and recirculation of the blood and reduces the surgical complexity associated with implanting other cardiac protheses.

It is another object of the present invention to provide a vehicular assist device with a reduced fluid conduit length, which further allows for the hydraulic fluid to be used not only to actuate the device and act as a bearing lubricant, but also to remove heat from the device and to disperse it via the lungs and the circulatory system.

It is still another object of the present invention to provide an electrohydraulic ventricular assist device having a design which allows for shorter electrical connections due to the integration of the major components.

It is a further object of the present invention to provide an electrohydraulic ventricular assist device which due to the configuration is suitable for use as a right, left or bi-ventricular device. This will result in a device which can be used in a wider range of patient population and diagnosis.

It is a further object of the present invention to provide an electrohydraulic ventricular assist device with a portion of the control electronics integrated into the back of the Unified System and the remainder of the control electronics to be provided on a small portable unit to be worn on a belt thus eliminating the requirement for tethering the patient to a large bulky external console to drive the device.

It is a further object of the present invention to provide a Unified System which can be secured to the rib cage to prevent migration and the resulting organ compression.

It is a further object of the present invention to provide a system which can be adapted to many different geometrical configurations to meet the requirements of different actuating means, within the overall constraints of the invention. This further allows for the use of the best possible actuating means and resulting geometry while retaining all the advantages of the present invention.

SUMMARY OF THE INVENTION

According to the present invention, there is provided a unified system for total implantation in the thorax of a patient and for cannulation to the circulatory system comprising: an internal electronic controller for generating an actuating signal; a blood pumping means with an inflow blood port and an outflow blood port for cannulation to the blood circulatory system; said pumping means displacing blood through said inflow and outflow ports in response to said actuating signal; and said unified system being contained within a housing the back of which has a convex surface curvature compatible with the internal human sagittal and transverse chest wall curvatures said housing containing a support for said internal electronic controller and containing said blood pumping means in a compact structure with said inflow and outflow ports oriented away from the front of said housing, and said structure having an overall size and geometry such that when the unified system is placed within the human thorax with the back of said housing adjacent the chest wall, said structure does not adversely compress adjacent organs, create dead space or limit chest closure.

In accordance with another aspect of the present invention, there is provided a unified system for total implantation in the thorax of a patient and for cannulation to the blood circulatory system comprising: an internal electronic controller for generating an actuating signal; actuating means for converting said actuating signal into a back and forth pulsating rhythmic displacement of a fluid; a blood pumping chamber having an inflow blood port and an outflow blood port for converting said back and forth displacement of said fluid into a rhythmic unidirectional displacement of blood through said inflow and outflow ports; hermetic coupling means for providing said internal electronic controller with a supply voltage; detecting means for detecting the status of said blood pumping chamber and accordingly generating a control signal to said internal electronic controller for synchronizing said actuating signal; a volume displacement chamber acting as a reservoir for said back and forth rhythmic displacement of a fluid; and a housing the back of which has a convex surface curvature compatible with the internal human sagittal and transverse chest wall curvatures for containing said internal electronic controller, said actuating means, said blood pumping chamber, said hermetic coupling means and said detecting means in a compact structure with said blood pumping chamber arranged with said inflow and outflow ports oriented away from the front of said housing and said structure having an overall size and geometry such that when the Unified System is placed within the human thorax with the back of said housing adjacent the chest wall, said structure does not adversely compress adjacent organs, create dead space or limit chest closure.

In a further aspect there is provided a Unified System for an electrohydraulic ventricular assist device adapted for implantation in the thorax and for cannulation to the blood circulatory system comprising: an internal electronic controller for receiving both an AC and DC supply voltages, an external communication channel data stream and generating an actuating signal, communication channel data stream and internal battery recharging signals; an actuating means for convening said actuating signal into a back and forth rhythmic displacement of a fluid; a blood pumping chamber having an inflow blood port and an outflow blood port for converting said back and forth displacement of said fluid into a rhythmic unidirectional displacement of blood through said inflow and outflow ports; a volume displacement chamber acting as a reservoir for said back and forth fluid displacement; a hermetic coupling means for connecting said controller by conductors carrying said AC/DC supply voltages, said communication channel data streams and internal battery recharging signal; a detecting means for generating said actuating signal in response to the status of said blood pumping chamber; and a housing the back of which has a surface curvature compatible with the internal human sagittal and transverse chest wall curvatures for containing said electronic controller, said actuating means, said blood pumping chamber, said hermetic coupling means and said detecting means in a compact structure with said blood pumping chamber arranged with said inflow and outflow ports (and one way valves) oriented away from the front of said housing and said structure with an overall size that when the Unified System is placed within the human thorax with the back surface of said housing adjacent the chest wall, said structure does not adversely compress adjacent organs.

According to another aspect of the present invention, there is provided a Unified System wherein the back of said housing has an average longitudinal radius of curvature of 22 cm±5 cm, and an average transversal radius of curvature of 10 cm±2 cm.

According to still another aspect of the present invention, there is provided a Unified System further comprising a first cannula connected to said inflow port for cannulation with the blood circulatory system. Said inflow port is oriented for cannulation to the systemic circulation when the Unified System is implanted in the thorax for assisting or replacing a left ventricle. The length of said first cannula is between 1 and 5 cm. A second cannula, which may have a length of between 5 and 14 cm, is connected to said outflow port is oriented for cannulation to the systemic circulation, when the Unified System is implanted to the thorax for assisting or replacing a left ventricle. Said inflow port is oriented for cannulation with the pulmonary circulation when said Unified System is implanted for assisting or replacing a right ventricle. Said outflow port is oriented for cannulation with the pulmonary circulation when said Unified System is implanted for assisting or replacing a right ventricle.

Acceding to still another aspect of the present invention, there is provided a Unified System having an overall thickness of less that 4 cm, an overall length less than 18 cm and an overall width less than 12 cm.

The device according to another aspect of the present invention is adapted for cannulation to the blood circulatory system and comprises: said Unified System for implantation in a human thorax proximal to the human heart to replace or assist a ventricle; a rechargeable internal battery for subcutaneous implantation to supply said Unified System with an internal DC supply voltage; an external battery for providing a DC voltage to an external controller; said external controller for converting DC voltage received from the external battery and/or external power supply to AC voltage for transfer by a transcutaneous energy transformer to power said Unified System, for recharging the external battery; a computer interface for connecting said device to a computer for control and monitoring of the device; a display means for control status and alarm display; a transcutaneous energy transformer for transmitting said AC voltage across the skin to said Unified System; a transcutaneous information telemetry system for bidirectional transmitting said communication channel data streams between said external controller and said Unified System; a connector for connecting said internal battery to said Unified System and an in-line connector for connecting said transcutaneous energy transformer to said Unified System.

The Unified System is totally implantable within the chest cavity and requires no physical connections (tubes and wires) through the skin to the outside of the body. The device is powered by either an implantable battery or a transcutaneous energy transfer system. The device is controlled and monitored remotely via a transcutaneous information telemetry or by said internal electronic controller. This will result in the elimination of potential infection sites caused by perforations in the skin.

According to the present invention, by integrating the major components in one unit, some components act as housings for other components. This will result in an overall reduction in amount of housing materials required, thus reducing the volume and weight which are major considerations in this type of device.

In addition, the device of the present invention to provide a so called Unified System which can be adapted for electrical, thermal, magnetic or mechanical actuation. This will result in the ability to select the best possible actuating means available at the time of design.

Anatomical fit has been a major limitation in artificial heart clinical success. Due to the size of these devices most are implanted in the abdomen or are outside the body. The volume, weight, geometrical configuration (dimensions and curvatures), integration of major components and placement are the main problems that this present invention addresses.

Advantageously, with the Unified System the major components are integrated into one unit capable of being implanted in the thoracic chest cavity, thus eliminating abdominal implantation and the need for abdominal surgery. Thus the diaphragm will not be penetrated and the implant will not cause problems for soft tissue organs in the abdomen such as the spleen, liver, intestine, etc. which are easily disturbed.

Another advantage of the Unified System comprises reducing the risk of infection by eliminating the need for direct physical access from outside of the body to inside by perforation of the skin. Placing the Unified System in the chest cavity further allows for anchoring to the chest cavity ribs, thus preventing critical organ damage, migration, infection and other complications associated with traditional abdominal implantation.

BRIEF DESCRIPTION OF THE DRAWINGS

These and other features of the invention will become more apparent from the following description in which reference is made to the appended drawings, wherein:

FIG. 7*a* is a general top view of another embodiment illustrating an alternative geometric configuration of the components;

FIG. 7*b* is a side view of the embodiment shown in FIG. 7*a;*

FIG. 8*a* is a general top view of another embodiment showing a further geometric configuration of the components;

FIG. 8*b* is a side view of the embodiment shown in FIG. 8*a;*

DESCRIPTION OF THE PREFERRED EMBODIMENT

Figure 1:
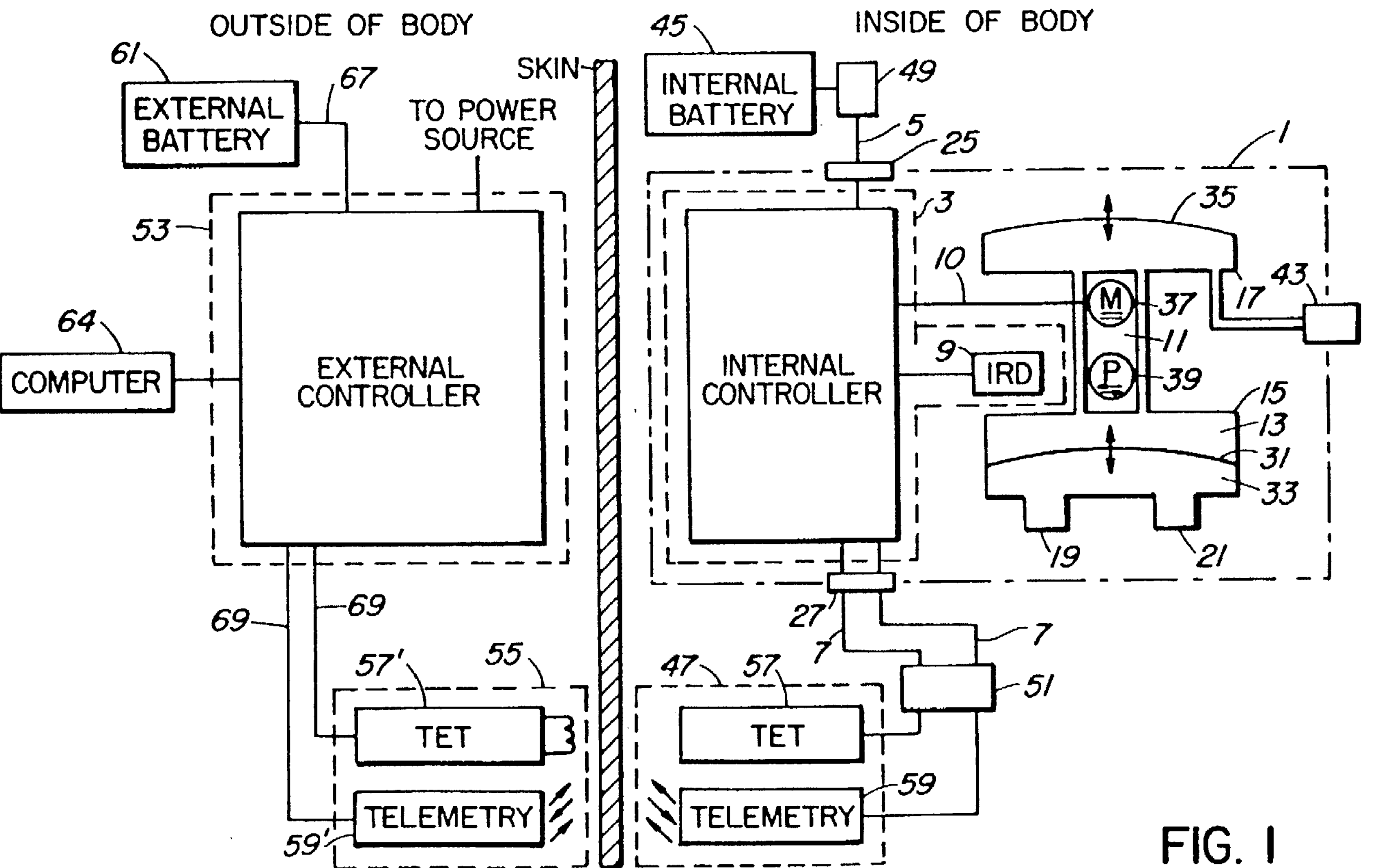
FIG. 1 illustrates a block diagram of the electrohydraulic ventricular assist device (VAD) of the present invention.

Referring to the drawings, a preferred embodiment of an electrohydraulic ventricular assist device in accordance with the present invention is described.

Figure 12:
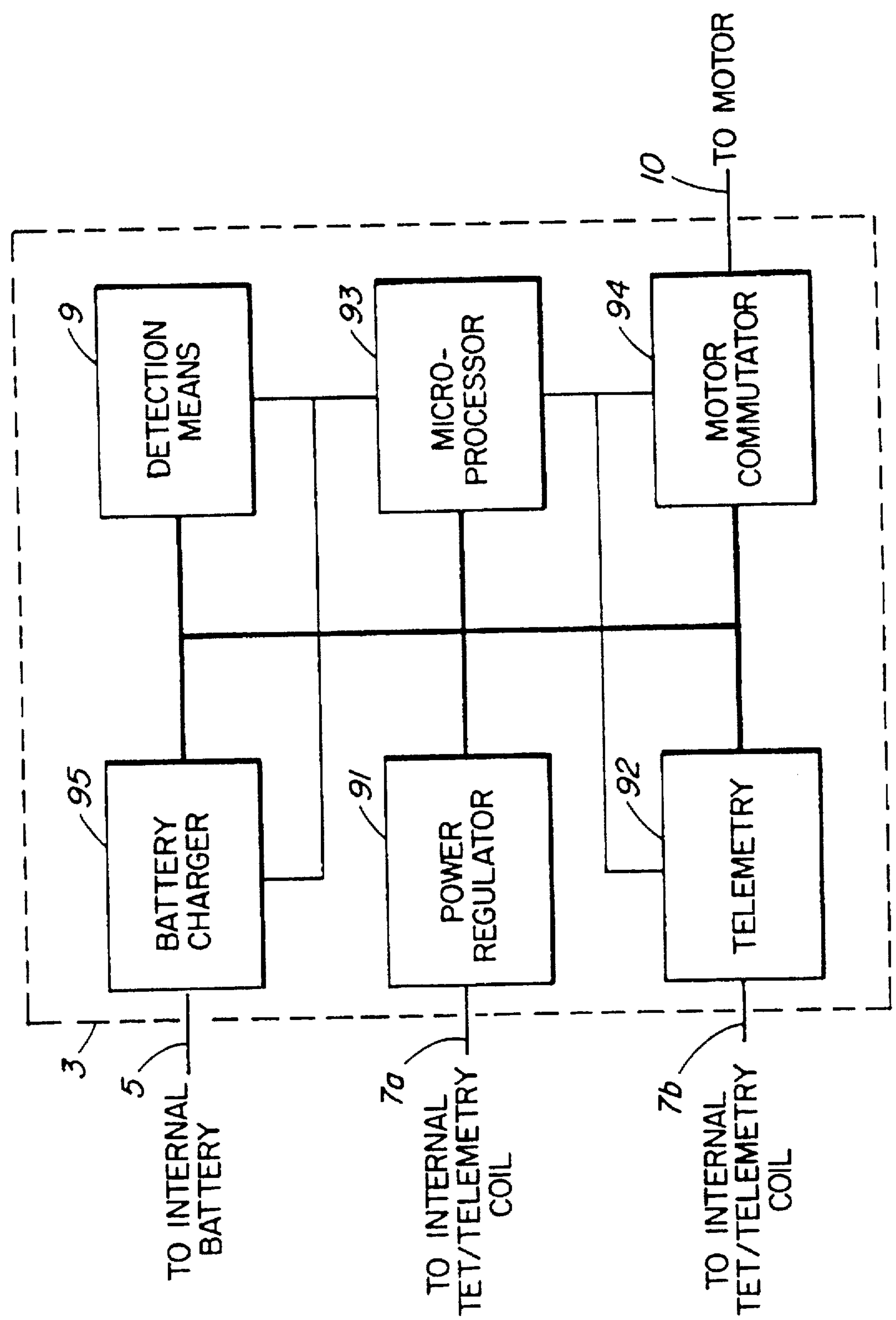
FIG. 12 is a detail diagrammatic view of internal electronic controller 3 shown in FIG. 1.

FIG. 1 illustrates a block diagram of the electrohydraulic ventricular assist device of the present invention. A Unified System 1 incorporates the major units of an electrohydraulic ventricular assist device and is sized for convenient implantation into the thorax and for facile cannulation to the blood circulatory system. The Unified System 1 comprises an internal electronic controller 3 which receives a DC supply voltage on conductor set 5, an AC supply voltage and communication channel data stream on conductor set 7 and signals from detecting means 9. The internal electronic controller 3 processes these signals and accordingly generates an actuating signal on conductor set 10. A functional block diagram of controller 3 is shown in FIG. 12.

Actuating means 11 converts the actuating signal from electronic controller 3 into a back and forth rhythmic displacement of a fluid, causing a rhythmic fill and drain of a fluid compartment 13 of a blood pumping chamber 15 with a fluid. A volume displacement chamber 17, diagrammatically shown in FIG. 1, acts as a reservoir for the fluid as it is displaced into and out of the fluid compartment 13. The blood pumping chamber 15 has an inflow blood port 19 and an outflow blood port 21. The blood pumping chamber converts the back and forth displacement of the fluid into a rhythmic unidirectional displacement of blood through the inflow and outflow ports.

The implantable components of the electrohydraulic ventricular assist device of the present invention consist of the Unified System 1, inflow and outflow cannulae, an internal battery 45 and an internal transcutaneous energy transformer (TET) telemetry unit 47 which may be of the type previously referred to on page 3.

The internal battery is connected to the Unified System 1 via hermetic connector 49, electrical conductor set 5 and electrical feedthrough 25, as shown in FIG. 1. The internal battery 45 is preferably implanted subcutaneously in the abdomen. In the preferred embodiment the internal battery package 45 uses rectangular prismatic nickel/cadmium cells, however other battery chemistries could be utilized. These cells are housed in a custom designed laser welded titanium enclosure with a hermetic connector 49 suitable for implantation. Preferably, the hermetic connector 49 is an internal connector, used for allowing an easy replacement of battery 45. In this way, the part of conductor set 5 from connector 49 through feedthrough 25 to Unified System 1, should not be changed when internal battery 45 is replaced periodically. The electrical conductor set 5 contains electrical connections for the supply of DC voltage to the internal electronic controller 3, for the recharging of the internal battery end for activation of an audible warning alarm housed in the battery enclosure.

The internal TET/Telemetry unit 47 is connected to the Unified System 1 via the in-line hermetic connector 51, electrical conductor set 7 and the electrical feedthrough 27. The internal TET/Telemetry unit 47 is implanted subclavicularly.

Figure 10:
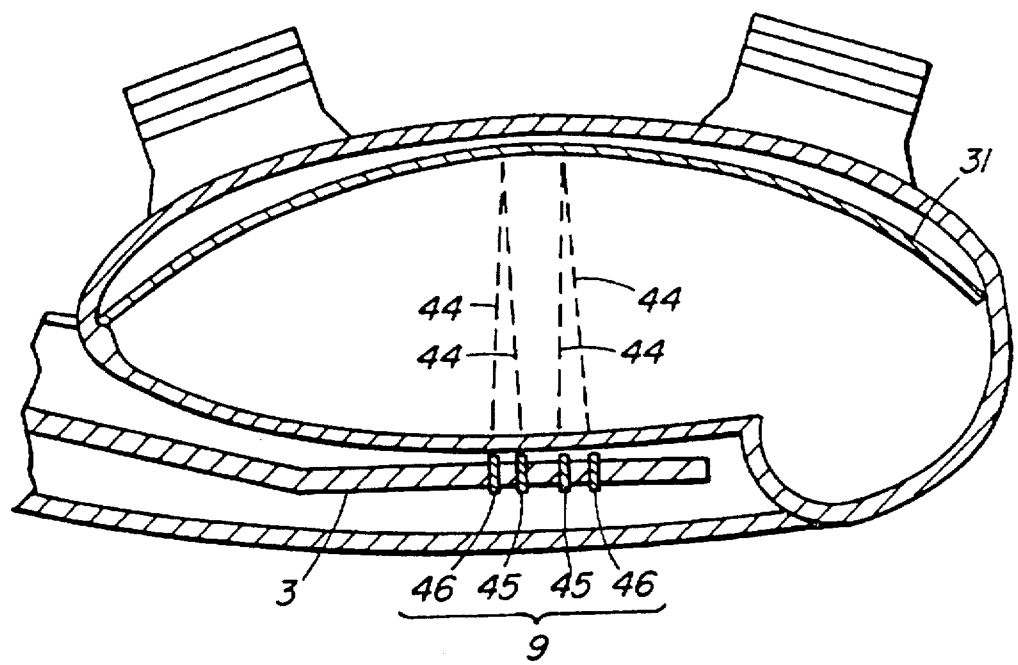
FIG. 10 is a detailed view of part of FIG. 6*b*, illustrating the detecting means 9.

The internal electronic controller 3 comprises a microprocessor which gives the actuating signal for reversing the direction of rotation of motor 37. Detecting means 9 detects the position of the flexible membrane 31 and generates a signal to the microprocessor to indicate when membrane 31 has arrived at the end systolic or end diastolic positions. Preferably, an infrared sensor is used as detector 9, which is provided directly on the internal controller and adjacent to the blood pumping chamber 15, as shown in FIG. 10.

A block diagram of the internal controller 3 is illustrated in FIG. 12. The signals transmitted by the external TET/telemetry unit 55 through the patient's skin are received by the internal TET/telemetry unit 47 and passed to power regulator 91 and telemetry system 92 over lines 7*a* and 7*b*. Power regulator 91 generates the DC voltage for supplying the circuits of the internal controller 3. The telemetry circuit 92 exchanges signals with the internal TET/telemetry unit 47 and with microprocessor 93. For example, an INTEL 87C196 may be used as microprocessor 93. Detection means 9 supervises the position of the membrane 31 and acknowledges when the membrane reached an extreme position. Detection means may be an infrared detector, but other detectors, as a magnetic type sensor, etc may be used. The microprocessor 93 processes the acknowledgement received from the detection means 9 and instructs a motor commutator unit 94 to generate the actuating signal on conductor set 10. The motor commutator unit 94 may be a MOTOROLA 33033 circuit. This signal reverses the rotation of motor 37 to accordingly pump the blood in and out of the blood pumping chamber 15. Microprocessor 93 exchanges information with the external computer through telemetry circuit 92. A battery charger 95 receives a battery charge control signal from the microprocessor 93 whenever the voltage on the internal battery 45 drops under a threshold level. Battery 45 is charged over conductor 5.

The external components of the electrohydraulic ventricular assist device of the present invention consist of the external electronic controller 53, an external battery 61 and an external TET/Telemetry unit 55, shown on FIG. 1.

The transcutaneous energy transformer (TET) and transcutaneous information telemetry (Telemetry) systems consist of electronic circuitry on both the internal electronic controller 3 and external electronic controller 53, the internal TET/Telemetry unit 47 and the external TET/Telemetry unit 55. The TET uses wire coils 57, 57' to electromagnetically couple power into the body without perforation of the skin. The Telemetry uses infrared components 59,59' embedded in the internal TET/Telemetry unit 47 and external TET/Telemetry unit 55 to transfer the communication channel data streams into and out of the body without perforation of the skin. The external TET/Telemetry unit 55 is connected to the external electronic controller 53 via electrical conductor set 69.

The external electronic controller 53 contains a portion of the circuitry for both the TET and Telemetry systems. External electronic controller 53 also produces and receives the communication channel data stream for control and monitoring of the Unified System 1 and generates recharging signals for recharging the external battery 61 at predetermined intervals. The external electronics is a compact unit intended to be worn on a belt similar to a pager.

Figure 11:
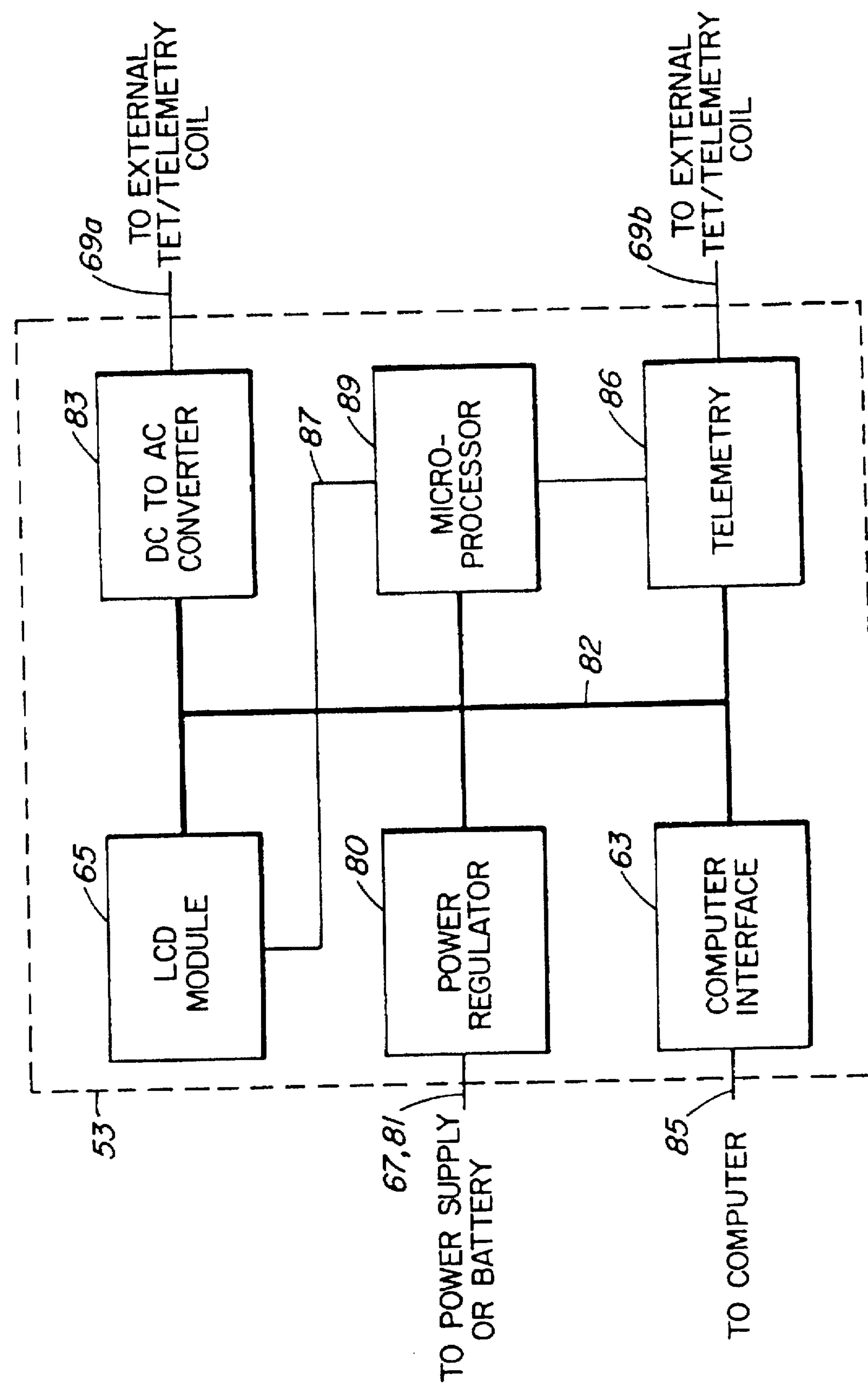
FIG. 11 is a detail diagrammatic view of external controller 53 shown in FIG. 1.

FIG. 11 illustrates diagrammatically in more detail the components of external controller 53 shown in FIG. 1. FIG. 11 shows a power regulator 80 which receives a DC or an AC supply from the mains power supply or from an external battery on input 67, 81. The connections 82 supply the other components shown in FIG. 11 with DC voltage. A DC to AC convertor 83 transmits an AC signal over conductor 69_a_ leading to external TET/telemetry unit 55. A computer interface 63 establishes the communication between the external controller 53 and the external computer 64 (shown in FIG. 1) over bus 85. Microprocessor 89 monitors a telemetry circuit 86 and LCD module 65. For example, an INTEL 87C196 may be used as microprocessor 89. Signals to and from the external TET/telemetry unit 55 are processed and communicated to the external computer 64 through interface 63. Various messages and warnings may be displayed on the LCD module 65, as programmed. Telemetry circuit 86 interface the signals exchanged between microprocessor 89 and external TET/telemetry unit 57, which in turn transmits these signals to internal TET/telemetry unit 47, and further to internal controller 3.

The external battery 61 is connected to the external electronic controller 53 via electrical conductor set 67. In the preferred embodiment the external battery uses silver/zinc cells, however other battery chemistries could be utilized. The electrical conductor set 67, 81 contains electrical connections for the supply of DC voltage to the external electronic controller 53 and for the recharging of the external battery 61.

FIGS. 2 to 6 illustrate the preferred embodiment of the implantable part of the electrohydraulic ventricular assist device which we refer to as the Unified System. Where possible, the same numerals as those used in schematic FIG. 1 have been employed.

Figure 2:
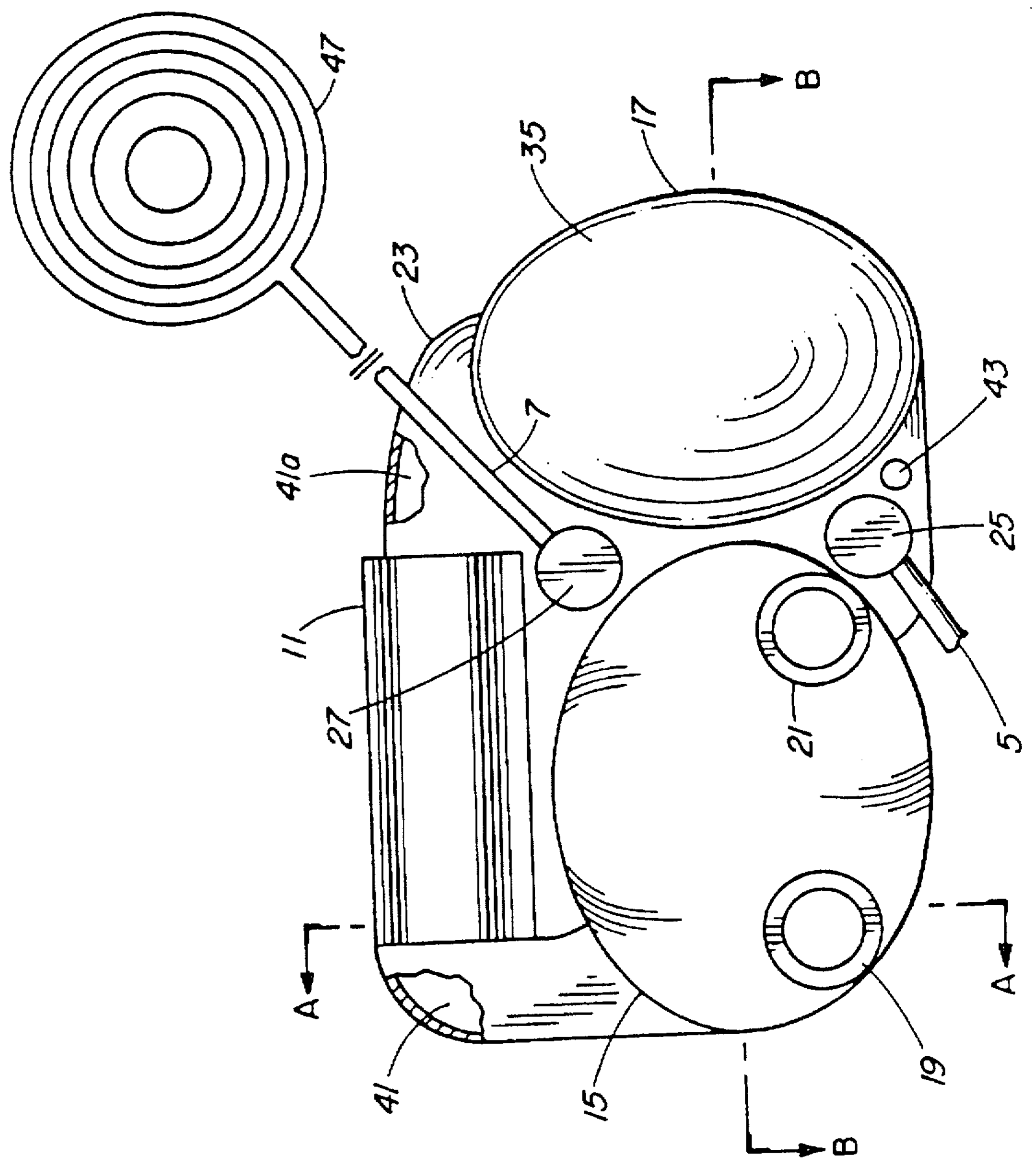
FIG. 2 is a front view of the implantable part of the VAD which will hereinafter be referred to as the Unified System, showing the surface facing the heart. Part is broken away to illustrate the fluid path.
Figure 5A:
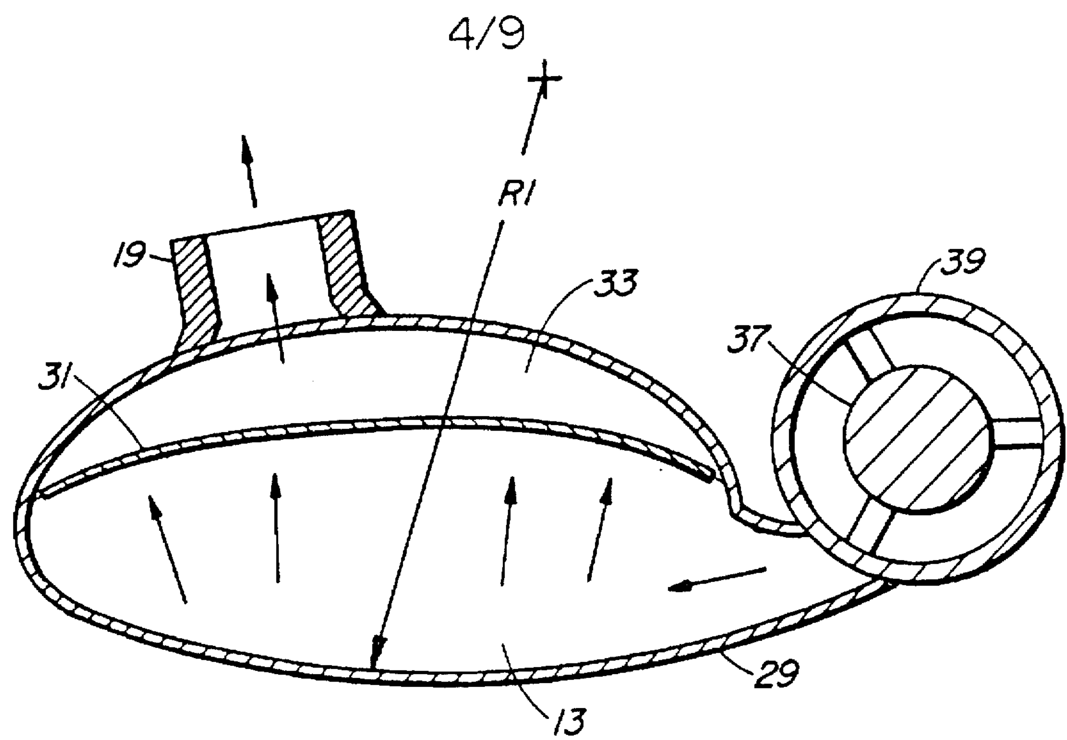
FIG. 5*a* shows a transversal cross-sectional view along lines A—A of FIG. 2, during the systolic phase of the cardiac cycle.
Figure 5B:
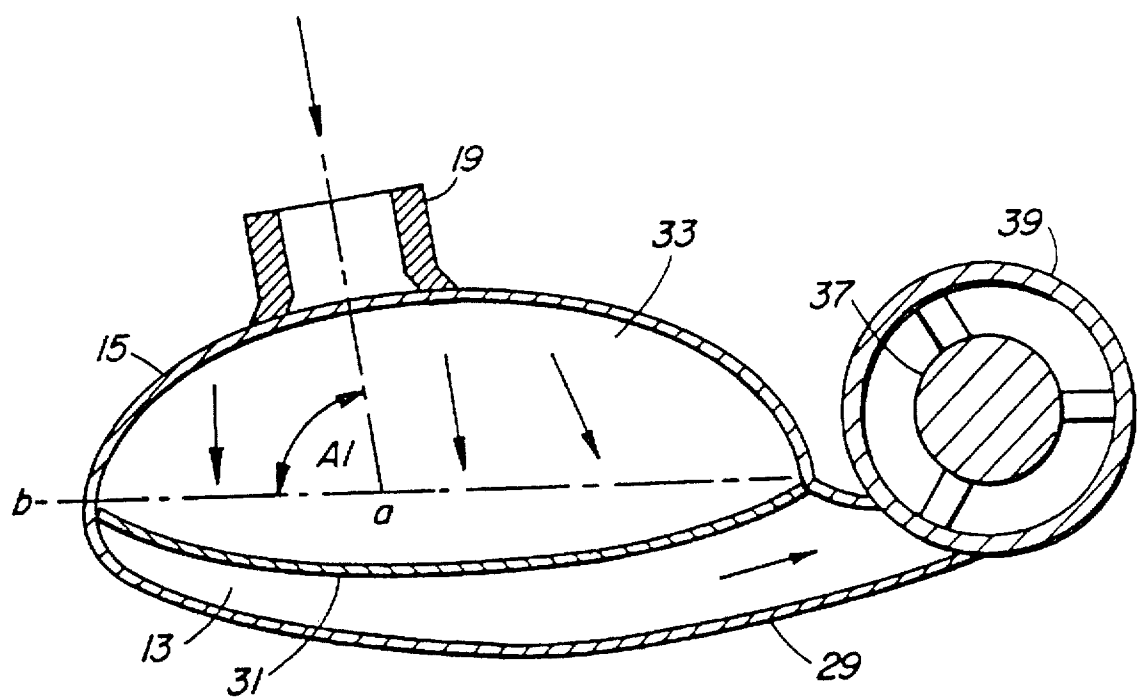
FIG. 5*b* shows a transversal cross-sectional view along lines A—A of FIG. 2, during the diastolic phase of the cardiac cycle.

In the front view FIG. 2, actuating means 11 which includes the motor 37 and the pump 39 (shown in FIGS. 5_a_ and 5_b_) causes hydraulic fluid to flow between reservoir 17 and fluid compartment 13 (which in FIG. 2 is behind blood pumping chamber 15 as apparent from FIGS. 5_a_ and 5_b_). The flow goes rhythmically backwards and forward through oil conduits 41 at one end of pump 39 communicating with compartment 13 and a short fluid conduit 41_a_ communicating between pump 39 and reservoir 17. Cover 23 in FIG. 2 is partly broken away to illustrate conduit 41_a_. Conduit 41 is broken away to show its interior.

Figure 6A:
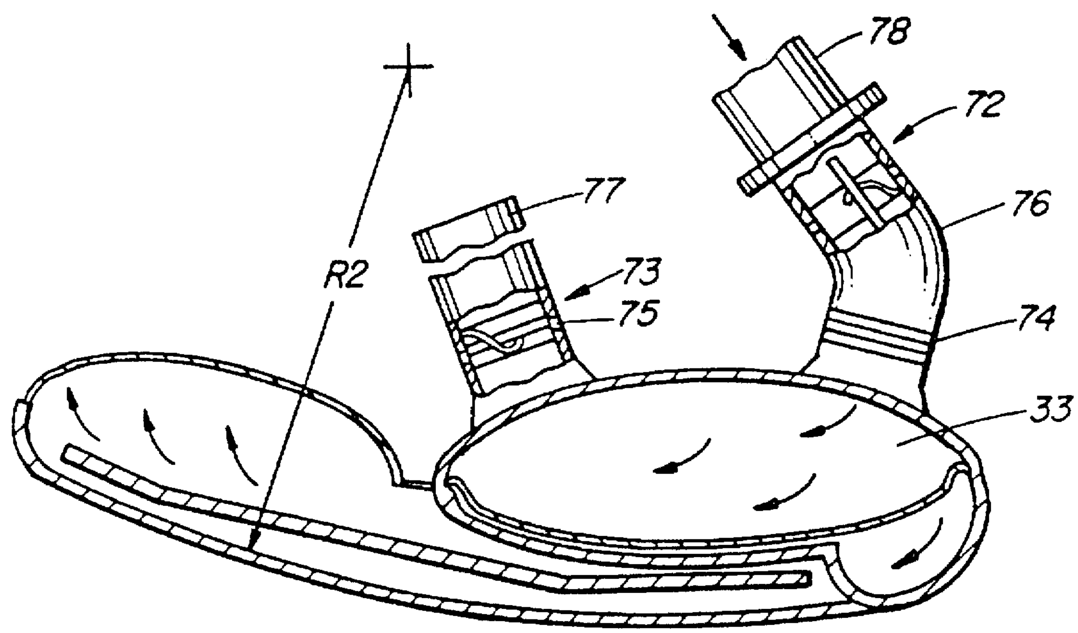
FIG. 6*a* shows longitudinal cross section view along lines B—B of FIG. 2, during the systolic phase of the cardiac cycle.
Figure 6B:
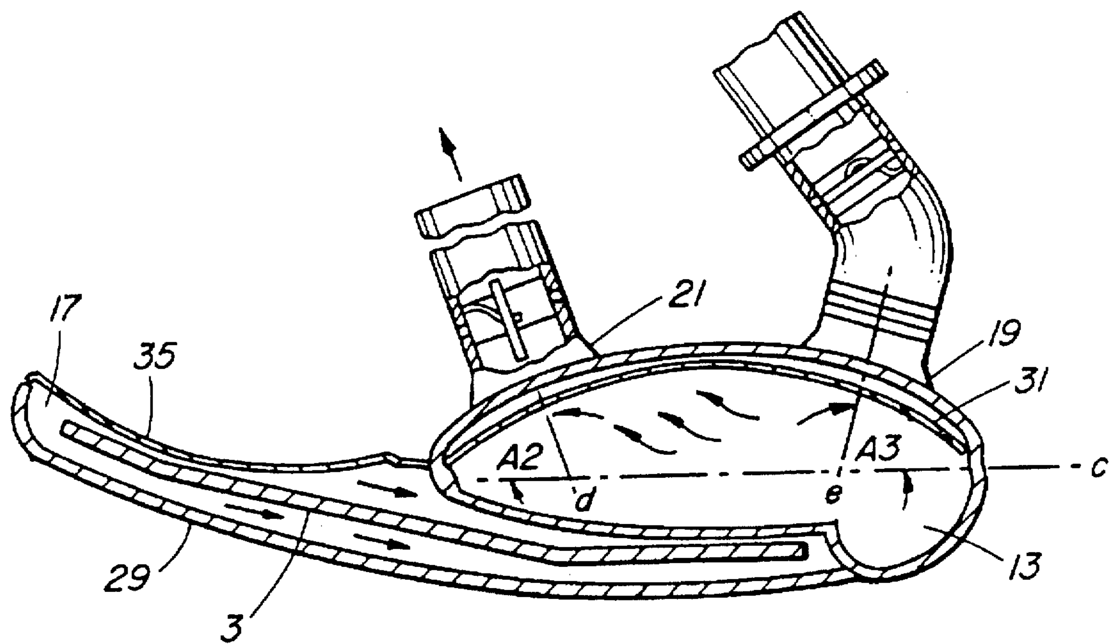
FIG. 6*b* shows longitudinal cross section view along lines B—B of FIG. 2, during the diastolic phase of the cardiac cycle.

FIG. 2 shows ports 19 and 21 which, as illustrated in FIGS. 6_a_ and 6_b_, have cannulae 76 and 77 joined to the inflow blood port 19 and outflow blood port 21 respectively. Within cannulae 76, and preferably close to port 19 there is a valve 72 which opens inwardly. An outwardly opening valve 73 is within cannula 77. The length of the outflow cannula 77 is preferably between 5 and 14 cm. The length of the inflow cannula 76 is between 1 and 5 cm. The shorter the distance, the better. Cannulae with appropriate valves are readily available commercially.

The Unified System 1 is connected to the systemic circulation when assisting the left ventricle or to the pulmonary circulation when assisting the right ventricle. The connection is through inflow and outflow cannulae 76 and 77 which include unidirectional valves 72 and 73 and rigid connectors 74 and 75. For left ventricular assist, the inflow cannula 76 is connected to the apex of the left ventricle through a scalloped tip 78 at the end of the cannula. The outflow cannula 77 consists of a small rigid connector in which the unidirectional valve sits and which is connected to a flexible cannula and ultimately is sewn to the aorta or to the corresponding blood vessels.

The unidirectional valves 72 and 73 may be any known valving apparatus which provide for substantially free flow of blood in one direction and substantially zero flow of blood in the opposite direction. Typical examples of such valves are disk, ball, bicuspid or tricuspid valves. The flexible cannulae 76 and 77 may be composed of a commercially available biostable material graft, such as a woven Dacron® graft (E.I. dupont de Nemours and Co. Inc.) while the rigid connectors are made from another commercially available biostable material, such as Tecoflex polyurethane (Thermedics Inc.).

The transversal angle $A_1$ in FIG. 5 between the axial centre line a of any of ports 19 and 21 and a base line b which is the approximate transverse centre line, may range from about 25° to 140°, but is preferably about 35°±10°. It is highly desirable that axial line a of the inflow port not be perpendicular to membrane 31 as otherwise there may be a tendency of the blood to clot with the potentiality of causing an embolism.

In FIG. 6 the longitudinal angle $A_3$ between the approximate longitudinal centre line c and axial line e of inflow port 19 may be between 25° to 140°, but is preferably about 130°±10°. The angle $A_2$ between baseline c and axial line d of outflow port 21 may be between 10° and 140°, but is preferably about 20°±10°. In each case, it is desirable that the axial lines of the ports not be perpendicular to the membrane 31.

The angles $A_1$ and $A_3$ determining the orientation of port 19 should be considered in combination so that the port has an anatomically convenient direction and also does not have an axis perpendicular to the membrane 31. Similarly, angles $A_1$ and $A_2$ of port 21 should be considered in combination. It is furthermore desirable that the axis of the inflow port not be perpendicular to the surface of cover 23.

Figure 3:
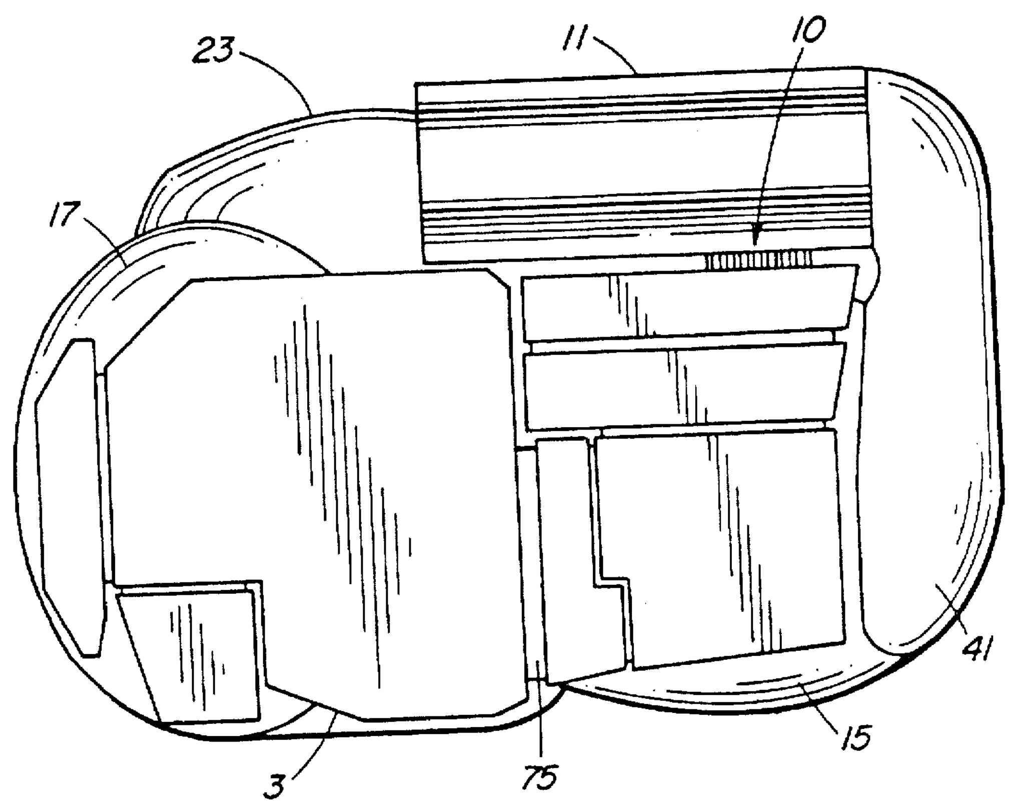
FIG. 3 is a back view of the Unified System shown in FIG. 2 with the back cover removed.
Figure 4:
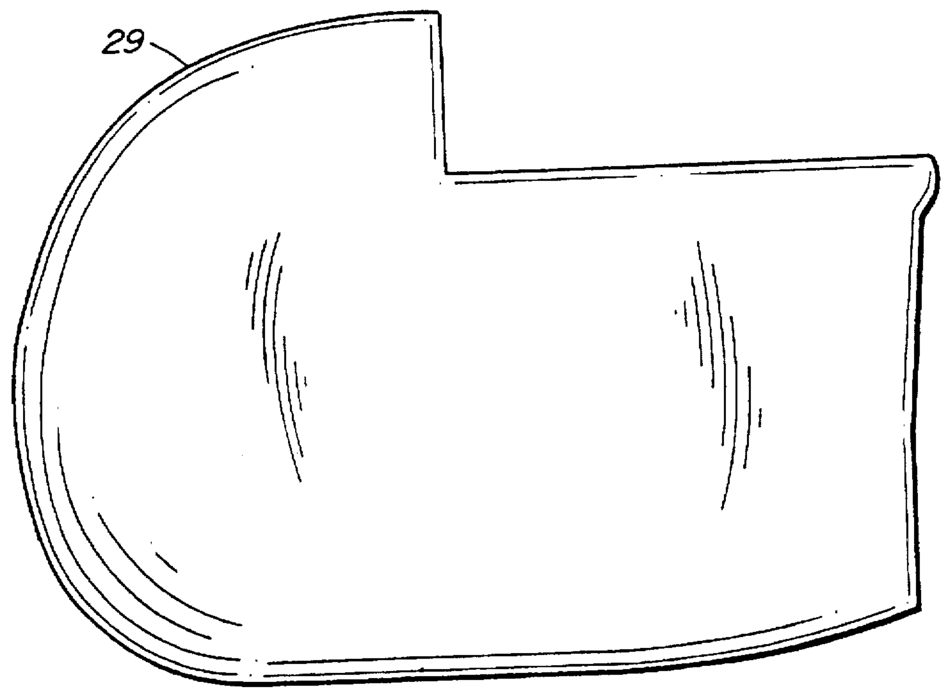
FIG. 4 illustrates a back view of the back cover removed from FIG. 3.

Hermetic coupling means, namely feedthrough cover 23, illustrated in FIGS. 2 and 3, houses electrical feedthroughs 25, 27 which connect to the conductors sets 5 and 7 carrying the DC supply voltage, AC supply voltage and communication channel data streams to the internal electronic controller 3 and units outside the Unified System 1. An oil filing port 43 is also mounted on feedthrough cover 23 for filling volume displacement chamber 17 with hydraulic fluid.

FIG. 3 illustrates a back view of the Unified System with the cover 29 (shown in FIG. 4) removed. The internal controller 3 is preferably segmented as exemplified by the bending lines 75 to provide some flexibility so that controller 3 can be substantially parallel to back cover 29 as shown in FIG. 6.

Cover 23, removable cover 29, conduit 41 and membrane 35 combine to provide a sealed housing containing the entire implantable Unified System.

In the preferred embodiment represented in FIGS. 5 and 6, the blood pumping chamber 15 has an elastomeric membrane 31 which converts the back and forth displacement of the fluid, driven by the actuating means 11, into the rhythmic displacement of the blood.

The shape of the blood compartment 33 is flat and low ellipsoidal, as a sac defining a back face and a front face, the back face being membrane 31, and the inflow and outflow ports 19 and 21 protruding through the front face. Membrane 31 divides the sac longitudinally in a plane normal to the axis of the blood pumping chamber 15 so that the height of the membrane oscillation is low. Membrane 31 defines a blood compartment 33 and a fluid compartment 13. The blood compartment 33 is comprised between the membrane 31 and the front face of blood pumping chamber 15. The fluid compartment 13 is comprised between membrane 31 and the back face of blood pumping chamber 15. Membrane 31 oscillates between a systolic position, where blood is displaced from the blood compartment and a diastolic position, where the blood compartment is filled with blood. The shape of the blood pumping chamber allows the membrane to travel a short distance between the systolic and diastolic positions, this short distance improves the mechanical properties of the membrane, thus increasing long term reliability. The systolic and diastolic positions of the membrane 31 and VDC membrane 35 are shown in FIGS. 5 and 6.

The actuating means 11 is a so called energy convertor. Energy convertor 11 converts the actuating signal received from the internal electronic controller 3 into a back and forth rhythmic displacement of the fluid. It comprises a brushless DC motor 37 and a reversible axial pump 39. Whenever motor 37 receives the actuating signal it reverses its rotation and accordingly the direction of fluid displacement by pump 39, converting this alternating rotational movement of the motor into a back and forth displacement of the fluid. The energy convertor 11 transfers fluid from the volume displacement chamber through the energy convertor 11 and through oil conduit 41 and **41*a* to the fluid compartment 13. As a result of this alternating fluid dislodgement the membrane 31 and VDC membrane 35 oscillate alternately between the systolic (blood being ejected from the device) and diastolic (blood entering the device) positions. The brushless motor 37** has bearings which have an axial preload to decrease ball skidding and thereby improve bearing life. The motor stator is a toothless design and the permanent magnet material is made of neodium iron boron which creates high magnetic field density.

The energy convertor 11 is arranged in the hydraulic fluid such that the hydraulic fluid is both a lubricant for the bearings in the energy convertor 11 and a heat sink. In the embodiment shown in FIGS. 1 to 6 the energy converter 11 is preferably placed towards the lower side of the Unified System, beside the blood chamber 15 to reduce the overall length of the fluid path. The oil conduit 41 provides a fluid pathway from one end of the energy convertor 11 to the fluid compartment 13 of the blood chamber 15 as shown in FIG. 3. The other end of the energy convertor opens substantially directly via passage **41*a* into the volume displacement chamber 17**.

As previously explained, detecting means 9 which is preferably an infrared sensor, monitors the position of membrane 31 and generates a signal to a microprocessor 93 forming part of internal electronic controller 3.

As illustrated in FIG. 10, detecting means 9 includes transmitters 46 which generate a signal illustrated by dotted line 44. This signal is reflected back by membrane 31 and received be receivers 45. The receivers 45 feed the signal to microcontroller 93 (see FIG. 12).

As shown in FIGS. 2, 5 and 6, the blood pumping chamber 15 and the volume displacement chamber 17 are placed side by side. These chambers define a space at the back thereof to accommodate the internal electronic controller 3 which is placed directly beside the energy convertor 11 and connected thereto, as illustrated at 10 in FIG. 3. This placement of the energy convertor 11 close to controller 3 allows short electrical connections, reduces electrical losses and increases the reliability and efficiency of the Unified System.

The operation of the device is now further described. The system is actuated by the hydraulic fluid that is pumped between the volume displacement chamber 17 and the fluid compartment 13 of blood pumping chamber 15, by the reversing axial flow pump 39 driven by the brushless DC motor. Whenever the motor 37 receives an actuating signal from the internal electronic controller 3, it reverses its direction of rotation which causes a reversal in the flow direction of the actuating fluid.

Actuating fluid is pumped into the fluid compartment 13 of the blood chamber 15 and the membrane 31 displaces the blood during the systole phase of the cardiac cycle through the outflow port 21. When the axial flow pump 39 is reversed, the hydraulic fluid is pumped away from the fluid compartment 13 of the volume displacement chamber 17, causing outward displacement of the VDC membrane 35, the membrane 31 is pulled away from the blood compartment 33 causing active filling of blood to occur through the inflow port 19. This action is further illustrated in FIGS. 5 and 6. Reversal points of the axial pump 39 are determined by the membrane position detector 9 which sends the status signal to the external electronic controller 3 for reversing the axial pump flow when the membrane 31 reaches the end points of systole and diastole.

The entire structure has an overall size and shape such that when the Unified System 1 is placed within the human thorax with the support 29 adjacent the chest wall, the Unified System does not adversely compress adjacent organs. The blood pumping chamber is arranged with the inflow and outflow ports 19 and 21 arranged such that the cannulae 76 and 77 are oriented towards their respective destinations of the blood circulatory system.

It is important that the dimensions of the human chest cavity be known for designing the shape and size of the Unified System. The space available for intra-thoracic placement of the device is very limited. The implantation site for the Unified System of the present invention is in the left and/or right hemithorax anchored to the chest wall between the 4th and 9th ribs. Advantages of this placement include limited device migration when fixed to the ribs, cosmetic acceptability, shorter cannulae lengths and therefore less hydraulic losses, less potential for kinking of the cannulae, no need to penetrate the diaphragm and elimination of risk of possible pressure necrosis of abdominal organs.

The size and shape of the back cover 29 are selected to snugly fit the geography of the ribs against which the device is arranged when implanted.

A prime consideration in the back cover design is the chest wall curvature. Any pockets formed between the device and chest wall would create dead spaces and a potentially increased risk of infection. The transverse radius of curvature of the intra-thoracic wall at the 5th rib was determined to be 9.4±0.5 cm (n=19) as disclosed by Mussivand T. et al. (Critical Anatomic Dimensions for Intrathoracic Circulatory Assist Devices, Journal of Artificial Organs, June 1992, Volume 16 #4).

Another important measurement in the design of the Unified System is the sagittal radius of curvature at the 5th rib. This was measured to be 11.1±0.5 cm. Knowledge of this dimension is necessary for the design of the longitudinal curvature of the device.

Back cover 29 has a longitudinal and transversal curvature to provide a convenient shape complementary to the thorax sagittal and transverse internal curvatures. The average longitudinal curvature of back cover 29 is illustrated in FIG. 6 as $R_2$, and is 22 cm±5 cm at the given section. The average transversal curvature of back cover 29 is illustrated in FIG. 5 as $R_1$, and is 10 cm±2 cm at the given section. In practice, the longitudinal radius of curvature of back cover 29 will be about radial centres that move a few centimeters from left to right of FIG. 6, so that at each end there is close conformity to the sagittal radius of curvature, but there will be some flattening intermediate its ends.

The Unified System of the present invention has an overall thickness of less than 4 cm, an overall length less than 16 cm and an overall external width less than 11 cm. It gives a cardiac output of greater than 8 liters/minute with a mean preload pressure of between 5 to 10 mm Hg and a mean afterload pressure of 150 mm Hg, with the Unified System of this invention, the stroke volume of the blood pumping chamber is between 55 and 70 ml.

Experimental Investigation

Anatomical

In order to determine the size and geometrical constraints of the Unified System for an intrathoracic placement, thoracic dimensions in cadavers and fit acceptability in live patients has been assessed to determine the acceptable size of the device for the present invention, some preliminary estimates of the size constraints in the left thoracic cavity were obtained using disc models of varying thickness and diameters. Disks with 2 cm to 6 cm thickness and diameters between 8 cm and 12 cm have been placed in the intended implant location of the left anterior chest wall of cadavers, after a chest wall incision. The maximum disk thickness and diameter that could fit into cadaver, without causing organ compression was recorded. Chest cavity dimensions were obtained during the autopsy of nineteen cadavers, eight within 24 hours of death and eleven preserved cadavers. A total of 19 cadavers were used for the experiments, the sizes are given in Table 1.

TABLE 1

| Cadavers | n | Height (cm) Mean ± SEM | Weight (kg) Mean ± SEM |
|---|---|---|---|
| Fresh | | | 65.6 ± 9.0 |
| Male | 4 | 175.0 ± 5.6 | 88.0 ± 4.6 |
| Female | 4 | 158.5 ± 4.2 | 43.2 ± 5.0 |
| Preserved | 11 | 174.8 ± 1.6 | 70.9 ± 4.6 |
| Male | 10 | 179.9 ± 1.4 | 73.7 ± 4.0 |
| Female | 1 | 165.0 | 45.0 |
| Total | 19 | 171.2 ± 2.3 | 68.5 ± 4.6 |

The cadaveric anatomical dimensions that were measured which are summarized in Table 2.

TABLE 2

| Anatomical Dimension | Distance (cm) Mean ± SEM | Range (cm) |
|---|---|---|
| Left ventricular apex to chest wall | 2.8 ± 0.3 | 1.5–3.5 |
| Midline anterior-posterior | 10.6 ± 0.6 | 6.0–14.5 |
| Root of the aorta to the diaphragm | 8.6 ± 0.4 | 7.0–10.0 |
| Sternum length | 18.9 ± 1.2 | 12.0–24.0 |
| Thorax width at 1st rib | 15.6 ± 1.2 | 10.5–21.0 |
| Thorax width at 5th rib | 24.6 ± 0.5 | 20.0–30.0 |
| Thorax width at 9th rib | 28.4 ± 2.2 | 18.0–35.0 |
| Midline to left lateral chest wall | 12.2 ± 0.7 | 9.5–14.0 |
| 4th–9th rib vertical midclavicle distance | 16.3 ± 1.8 | 12.0–22.0 |
| Sagittal radius of curvature at 5th rib | 11.1 ± 0.5 | 9.0–12.0 |
| Transverse radius of curvature at 5th rib | 9.4 ± 0.5 | 8.5–10.0 |

The most critical dimension that defines the configuration of the device was the ventricular apex to the chest wall which was found to be 2.8±0.3 cm. The sagittal radius of curvature at the 5th rib was found to be 11.1±0.5 cm and the transverse radius of curvature at the 5th rib was found to be 9.4±0.5 cm.

An epoxy model of one of the Unified System configurations was made based on these cadaveric anatomical dimensions. In addition, six sterilizable epoxy version models of this design were available for intraoperative fit trials. Following informed consent, the prototype models were placed in the left chest cavity in patients varying in weight from 65 to 100 kilograms and heights from 155 to 190 centimeters who ware undergoing various cardiac procedures.

Figure 9:
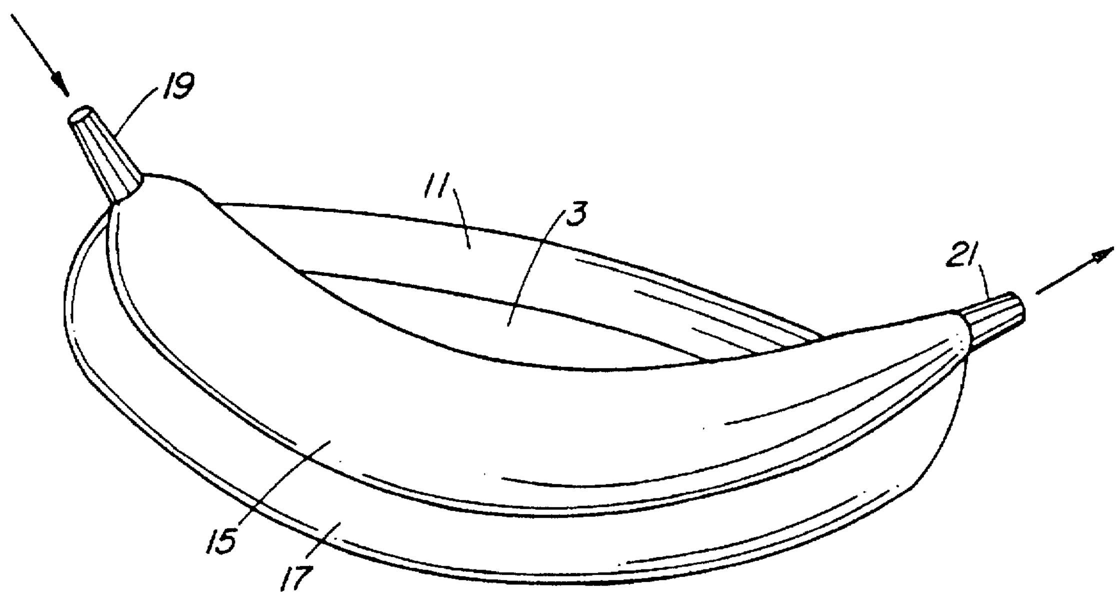
FIG. 9 is a general top view of mother embodiment showing a further geometric configuration of the components.

The following was concluded based on the cadaver fit trials and intraoperative patient fit trials:

1. That a model having a thickness of less than 4 cm and a diameter of 11 cm with a sagittal and transverse curvature of 11.5 and 9.4 could be accommodated in the intrathoracic cavity of the cadavers studied without significant compression of vital structures such as the heart and left pulmonary hilus.
2. That with intrathoracic positioning of the device, outflow cannulation could be routed anteriorly over the lungs to the root of the ascending aorta. The length of the inflow cannulation would be very short due to its proximity to the left/right ventricular apex.
3. That the size of the device could be no larger than 18×12×4 cm for the size of human bodies studied.
4. That various geometrical configurations of the device are feasible provided that they are within the size and shape constraints outlined above. Some of these different geometrical configurations are illustrated in FIGS. 7, 8, and 9.

In Vitro

Testing was conducted in vitro to verify that the system operated satisfactorily prior to any in vivo experiments. Tests have been conducted on mock circulation with the device in air and completely submerged in saline solution to simulate expected chest pressures. In vitro flow rates of over 8 liters per minute with a proload of 10 and a mean afterload of 100 mm Hg have been obtained. The transcutaneous energy transformer has demonstrated a power transfer efficiency of over 80% at power levels of 10–35 Watts. The internal and the external batteries have been cycled tested to determine optimum charge and discharge requirements as well as to determine operating times and cycle lives.

In Vivo

The complete Unified System has been implanted in 10 bovine for in vivo testing and has maintained circulation from 3 to 96 hours. The performance of the complete Unified System has proven satisfactory in acute experimentation. The overall configuration of the device has also proven to be satisfactory, over a wide range of operating conditions.

Other Geometric Arrangements

Geometric arrangements other than those shown in FIG. 2 to 6 may prove to be desirable. FIGS. 7*a* and 7*b* illustrate one such arrangement designed to give a short hydraulic path. Numerals the same as those used in FIGS. 1 to 6 have been employed. FIG. 7*a* is a top view and FIG. 7*b* is a side view. The actuator 11 is controlled by control electronics 3 to cause hydraulic fluid to flow from volume displacement chamber 17 to cause blood in blood chamber 15 to be pumped entering at inflow blood port 19 ad exiting at outflow blood port 17.

FIG. 8*a* is a top view and FIG. 8*b* is a side view of another geometric configuration in which the control electronics 3 is located between blood chamber 15 and volume displacement chamber 17.

FIG. 9 is a perspective view of a configuration where the blood chamber 15 is adjacent to volume displacement chamber 17 both of which are approximately arcuately shaped.

I claim:

1. A unified system for use in a ventricular assist device and for total implantation in a thorax of a patient for cannulation to the blood circulatory system to replace or assist a ventricle of a natural heart of the patient, said unified system comprising:
  - an internal electronic controller for generating an actuating signal;
  - a blood pumping means provided proximate to said internal electronic controller, said blood pumping means comprising:
    - a blood pumping chamber comprising:
      - a blood compartment having an inflow blood port and an outflow blood port for cannulation to the blood circulatory system;
      - a fluid compartment for receiving a fluid; and
      - a flexible membrane separating said blood compartment and said fluid compartment;
    - a volume displacement chamber for receiving the fluid;
    - a fluid conduit connecting said blood pumping chamber and said volume displacement chamber to allow flow of the fluid between said blood pumping chamber and said volume displacement chamber; and
    - an actuating means, provided in said fluid conduit, for converting said actuating signal into a pulsating rhythmic displacement of the fluid between said blood pumping chamber and said volume displacement chamber through said fluid conduit and said actuating means;
  - wherein said actuating means is provided proximate to said internal electronic controller, said blood pumping chamber and said volume displacement chamber so that said unified system has a shape with a convex back surface having a curvature compatible with curvatures of an internal human sagittal and transverse chest wail, and an overall size and geometry such that, when the unified system is implanted in the patient, said unified system is accommodated within the thorax with the back surface of said unified system adjacent the chest wall without adversely compressing adjacent organs, creating dead space or limiting chest closure.

2. A unified system as claimed in claim 1, wherein the back surface of said unified system has longitudinal curvature complementary to a sagittal radius of 11±0.5 cm and a transversal curvature complementary to an intrathoracic wall having a radius of 9.4±0.5 cm.

3. A unified system as claimed in claim 2 in which the average transversal radius of curvature of the back of said unified system is 10±2 cm and the average longitudinal radius of curvature is 22±5 cm.

4. A unified system as claimed in claim 1, wherein said blood ports are equipped with one-way valves to ensure unidirectional flow of blood from the natural heart through said blood chamber to the systemic and/or pulmonary circulation systems.

5. A unified system as claimed in claim 1, further comprising an inflow cannula connected to said inflow port and an outflow cannula connected to said outflow port for cannulation with the blood circulatory system.

6. A unified system as claimed in claim 5, wherein said inflow port is oriented at a longitudinal angle $A_3$ between 25° and 140° and at a transversal angle $A_1$ between 25° and 140° with respect to longitudinal and transverse centre lines respectively of said unified system, so as to minimize the distance between said inflow port and the systemic or pulmonary circulation when the unified system is implanted in the thorax for assisting or replacing a respective ventricle and in which none of said angles makes the axis of the inflow port perpendicular to said membrane.

7. A unified system as claimed in claim 5 in which $A_1$ is 35°±10° and $A_3$ is 130°±10°.

8. A unified system as claimed in claim 7 in which $A_1$ is 35°±10° and $A_2$ is 20°±10°.

9. A unified system as claimed in claim 5, wherein the length of said outflow cannula is between 5 and 14 cm.

10. A unified system as claimed in claim 5, wherein said outflow port is oriented at a longitudinal angle $A_2$ between 10° and 140° and at a transversal angle $A_1$ between 25° and 140° with respect to longitudinal and transversal centre lines respectively of said unified system, so as to minimize the distance between said outflow port and the systemic or pulmonary circulation when the unified system is implanted in the thorax for assisting or replacing a respective ventricle.

11. A unified system as claimed in claim 5, wherein the length of said inflow cannula is between 1 and 5 cm.

12. A unified system as claimed in claim 1, having an overall thickness of less than 4 cm.

13. A unified system as claimed in claim 1, having an overall length less than 18 cm.

14. A unified system as claimed in claim 1, having an overall width less than 12 cm.

15. A unified system as claimed in claim 1, wherein said inflow port is provided with a first one way valve which allows entry of blood into said blood compartment and said outflow port is provided with a second one-way valve which allows ejection of the blood from said blood compartment.

16. A unified system as claimed in claim 1, wherein the stroke volume of said blood pumping chamber is between 55 and 70 ml.

17. A unified system as claimed in claim 1, giving a cardiac output of greater than 3 liters/minute with a mean preload pressure of between 5 to 10 mm Hg and an afterload pressure greater than 100 mm Hg.

18. A unified system as claimed in claim 1, wherein said actuating means comprises:
  - a brushless DC motor for receiving said actuating signal and converting it into a forward and reverse rotational movement;
  - a reversible axial pump for converting said rotational movement into said back and forth displacement of fluid to displace said flexible membrane between systolic and diastolic positions.

19. A unified system as claimed in claim 18, wherein said motor and said pump form a unitary energy convertor.

20. A unified system as claimed in claim 19, wherein said fluid further acts as a lubricant for bearings in said energy convertor and as means to disperse heat from the actuating means and the internal electronic controller throughout the device to minimize tissue necrosis due to heat.

21. A unified system as claimed in claim 18, comprising detecting means for detecting the systolic or diastolic position of said flexible membrane and for accordingly generating a control signal to said internal electronic controller for synchronizing said actuating signal with the displacement of said flexible membrane.

22. A unified system as claimed in claim 21, wherein said detector is an infrared sensor.

23. A device as claimed in claim 1, further comprising means for securing said support to a rib cage to prevent migration and the resulting organ compression.

24. A unified system as claimed in claim 1 further comprising a support for said internal electronic controller and said blood pumping means so that said inflow and outflow ports are oriented away from a front surface of said unified system.

25. A unified system as claimed in claim 1, wherein said blood pumping chamber converts said pulsating rhythmic displacement of the fluid into a rhythmic unidirectional displacement of blood into and from said blood compartment through said inflow and outflow ports.

26. A unified system as claimed in claim 1, wherein said internal electronic controller has a first set of conductors for providing said internal electronic controller with a supply voltage, and said unified system further comprises a feedthrough cover for hermetic trespass of said first set of conductors.

27. A unified system as claimed in claim 26, wherein said feedthrough cover further comprises a fluid port for filling said volume displacement chamber, said fluid compartment and said fluid conduit with fluid.

28. A unified system as claimed in claim 1, wherein said blood pumping chamber comprises a generally flat oval sac defining a back face and a front face, and said inflow and outflow ports protrude from said front face;

said flexible membrane divides said sac longitudinally to define said blood compartment between said front face and said flexible membrane, and said fluid compartment between said flexible membrane and said back face;

said flexible membrane oscillates between a systolic position, to displace blood from blood compartment into the circulatory system, and a diastolic position, to fill up said blood compartment with blood from the circulatory system;

said pulsating rhythmic displacement of the fluid generates said oscillating displacement of said flexible membrane between said systolic position, where the fluid is displaced in said fluid compartment, and said diastolic position, where the fluid drains off said fluid compartment.

29. A unified system for use in a ventricular assist device and for total implantation in a thorax of a patient for cannulation to the blood circulatory system to replace or assist a ventricle of a natural heart of the patient, said unified system comprising:

an internal electronic controller for generating an actuating signal;

a blood pumping means provided proximate to said internal electronic controller, said blood pumping means comprising:

a blood pumping chamber comprising:

a blood compartment having an inflow blood port and an outflow blood port for cannulation to the blood circulatory system;

a fluid compartment for receiving a fluid; and a flexible membrane separating said blood compartment and said fluid compartment;

a volume displacement chamber for receiving the fluid;

a fluid conduit connecting said blood pumping chamber and said volume displacement chamber to allow flow of the fluid between said blood pumping chamber and said volume displacement chamber; and an actuating means, provided in said fluid conduit, for converting said actuating signal into a pulsating rhythmic displacement of the fluid between said blood pumping chamber and said volume displacement chamber through said fluid conduit and said actuating means;

hermetic coupling means for providing said internal electronic controller with a supply voltage; and detecting means for detecting the status of said blood pumping chamber and accordingly generating a control signal to said internal electronic controller for synchronizing said actuating signal with the status of said blood pumping chamber;

wherein said actuating means is provided proximate to said internal electronic controller, said blood pumping chamber and said volume displacement chamber so that said unified system has a shape with a convex back surface having a curvature compatible with curvatures of an internal human sagittal and transverse chest wall, and an overall size and geometry such that, when the unified system is implanted in the patient, said unified system is accommodated within the thorax with the back surface of said unified system adjacent the chest wall without adversely compressing adjacent organs, creating dead space or limiting chest closure.

* * * * *